United States Patent [19]

Nazareth et al.

[11] 3,968,122

[45] July 6, 1976

[54] 1-ACETYL-3-N-OCTANOYL-5-ETHYLIDENE TETRAMINIC ACIDS AND METAL SALTS THEREOF

[75] Inventors: Julia Nazareth; Naren M. Gandhi; Pandurang V. Divekar; Noel J. de Souza; Hans Kohl, all of Bombay, India

[73] Assignee: Hoechst Aktiengesellschaft, Frankfurt am Main, Germany

[22] Filed: Aug. 15, 1974

[21] Appl. No.: 497,719

[30] Foreign Application Priority Data

Oct. 19, 1973  Germany............................ 2352448

[52] U.S. Cl. ..................... 260/326.5 FL; 195/81; 260/501.1; 424/274
[51] Int. Cl.[2] ............... C07D 207/00; C07D 207/12; C07D 207/24
[58] Field of Search ........................... 260/326.5 FL

[56] References Cited
UNITED STATES PATENTS 3,692,775  9/1972  Kubanek et al. ............ 260/326.5 FL
3,708,473  1/1973  Collins ..................... 260/326.5 FL

*Primary Examiner*—Dale R. Ore
*Attorney, Agent, or Firm*—Curtis, Morris & Safford

[57] ABSTRACT

Magnesidin, which comprises a mixture of the compounds of the general formula I

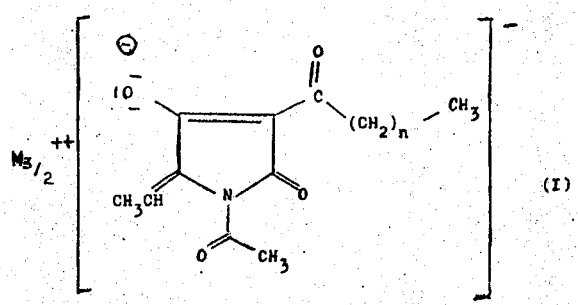

in which $n$ is the integer 4 or 6, the magnesium-free form of Magnesidin, and the salts thereof with mono- or polyvalent cations, and a process for the preparation of Magnesidin which comprises cultivating pseudomonas magnesiorubra HPL No. Z-1190 (ATCC 21.856).

7 Claims, No Drawings

1-ACETYL-3-N-OCTANOYL-5-ETHYLIDENE TETRAMINIC ACIDS AND METAL SALTS THEREOF

The present invention relates to a new antibiotic containing magnesium, hereinafter called "Magnesidin", to the magnesium-free form of the antibiotic and the salts thereof, as well as to a process for its manufacture, isolation and purification.

The new antibiotic may be obtained by cultivating the bacterium Pseudomonas magnesiorubra sp. nov. HPL No. Z-1190 (in American Type Culture Collection, Rockville, Maryland, U.S.A., registered under ATCC No. 21.856). The strain was isolated from the surface of *Caulerpa peltata*, a species of algae collected on a rocky shore near Bombay, India.

The bacterium Pseudomonas magnesiorubra or its variants and mutants may be cultivated according to the usual microbiological methods, such as surface or submersion cultivation methods, in shaking flasks and fermenting containers using nutrient media which are generally known for the cultivation of microorganisms.

In addition to the surface and submersion methods, continuous cultivation methods may also be employed.

The antibiotic Magnesidin may be isolated from the cell mass of Pseudomonas magnesiorubra according to the methods disclosed below.

The bacterium is identified on the basis of its morphological and physiological properties. As for the taxonomia, it belongs to the genus Pseudomonas (family of Pseudomonadaceae). Since it differs from all Pseudomonas species classified in Bergey's manual of Determinative Bacteriology (The Williams & Wilkins Co., 7th Edition, 1957, pages 90 to 96), the culture was given the name "*Pseudomonas magnesiorubra*".

The morphological and physiological properties of Pseudomonas magnesiorubra sp. nov. are mentioned in the following Table I.

TABLE I

Characteristic morphological and biochemical properties of Pseudomonas magnesiorubra (ATCC No. 21.856)

| Properties | observations/results |
|---|---|
| Morphological | |
| cell size (microns) | 0.8 – 1.0 × 1.6 – 2.6 |
| flagellation | polar |
| Biochemical and physiological | |
| Growth in medium | |
| distilled water | weak |
| sea water | + |
| milk | + |
| 12 – 30 % salt solutions | – |
| Hydrolysis of | |
| casein | + |
| gelatin | + |
| starch | + |
| Reduction of nitrates | + |
| Production of acetoin | – |
| Production of indole | – |
| Production of $H_2S$ | – |
| Degradation of cellulose | – |
| Acid formation from | |
| arabinose | – |
| glucose | + |
| galactose | + |
| lactose | – |
| maltose | + |
| sucrose | + |
| raffinose | – |
| trehalose | – |
| mannitol | + |
| sorbitol | – |
| dulcitol | – |
| salicin | + |
| Test for oxidase according to Kovač | + |
| Production of pigments | produces prodigiosine |

TABLE I-continued

Characteristic morphological and biochemical properties of Pseudomonas magnesiorubra (ATCC No. 21.856)

| Properties | observations/results |
|---|---| and its higher homologs.

The process of the invention relates to the cultivation of strains of Pseudomonas magnesiorubra (ATCC 21.856) at temperatures preferably of from about 20° to 40°C in a nutrient solution containing suitable carbon and nitrogen sources and preferably, one or more nutrient salts and/or trace elements. Such a nutrient medium may contain glucose, sucrose, starch or a different carbohydrate source as well as peptone, tryptone, meat and yeast extracts, soya bean flour and the like, in addition to inorganic salts. The nutrient salts preferably contain, for example sodium, potassium, magnesium, calcium, phosphorus and sulfur. The trace elements mentioned are especially, for example iron, manganese and zinc. Examples are sodium chloride, magnesium sulfate and potassium hydrogeno-orthophosphate. Instead of these complex nutrient solutions, synthetic nutrient media containing glycerol, glutamic acid, proline, leucine, isoleucine, aspartic acid, inorganic salts and the like may also be added. Large-scale cultivation of Pseudomonas magnesiorubra is preferably effected according to the submersion method under aerobic conditions at about 28° to 30°C. The pH-value of the nutrient medium should range from about 5 to 9, preferably from 7 to 7.5. The cultivating process is discontinued after 12 to 24 hours after optimum yields of Magnesidin have been obtained. The cell mass then contains a considerable amount of Magnesidin.

To isolate the antibiotic Magnesidin, the cell mass is separated from the culture solution by centrifuging, washed with water and extracted with a suitable organic solvent, for example hot acetone, methanol or ethanol. The organic solvent containing the antibiotic is then separated by centrifuging or filtering it.

The cells of Pseudomonas magnesiorubra may also be destroyed by known methods and the antibiotic may be extracted or precipitated by means of a solvent, for example petroleum ether, benzene, acetone or butanol.

The solvent extracts containing Magnesidin are decolored using charcoal and concentrated in vacuo to a small volume. The crude Magnesidin separates as an amorphous powder when cool (while cooling). The precipitated antibiotic is suction-filtered and may be recrystallized from methanol or acetone, upon the decoloration operation by means of charcoal, to yield Magnesidin in pure form.

The major amount of the antibiotic Magnesidin is contained in the bacterium's cell mass of Pseudomonas magnesiorubra. The small amounts of anitbiotic in the culture liquor may, however, also be recovered by extracting it with a suitable solvent which is not miscible with water, such as diethyl ether, ethyl acetate, or butanol.

The new antibiotic Magnesidin, which differs in its chemical and physical properties from the rest of antibiotics hitherto disclosed in the literature, is a colorless neutral substance. It is soluble in ether, ethyl acetate, chloroform, acetic acid, methanol, ethanol, butanol, pyridine, dimethylformamide, and dimethyl-sulfoxide, but is insoluble in water.

The term Magnesidin includes the magnesium salts of an about equivalent mixture of 1-acetyl-3-n-hexanoyl-5-ethylidene-tetraminic acid and of 1-acetyl-3-n-octanoyl-5-ethylidene-tetraminic acid of the formula I

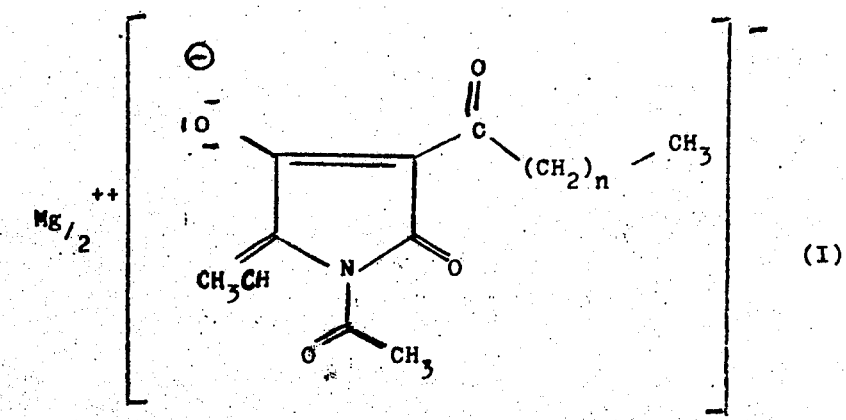

in which n stands for the integer 4 or 6, which can be established for example by mass spectrometry of magnesium-free Magnesidin derivatives. Magnesidin can be separated into two compounds, for example by means of thin-layer chromatography using kieselguhr plates having a thickness of 0.25 mm, which are coated with paraffin and are developed with a mixture of acetic acid and water (4 : 1) and treated with 5% iron trichloride in 0.5 N hydrochloric acid for vizualizing purposes. When sprayed with iron trichloride, the two compounds give a reddish brown color which is a characteristic of compounds having an enol structure, as has Magnesidin. When sprayed with 2,4-dinitrophenyl hydrazine, the two compounds also show an orange-yellow color which is a characteristic of compounds having a carbonyl group, as has Magnesidin. The $R_f$-values of the two compounds vary slightly as a function of the physical parameters under which thin-layer chromatography is carried out. The average $R_f$-values obtained from eight determinations of the two compounds range from 0.60 to 0.77.

The two separated compounds have almost the same biological activity as has Magnesidin.

The antibiotic Magnesidin has no definite melting point. At 123°C it begins to shrink, it gets soft when the temperature rises to 150°C and remains then unchanged up to a temperature of 300°C. The antibiotic has no optical activity either.

When developed on thin-layer chromatography plates, 0.20 mm thick, made of silica gel $F_{254}$ on aluminum foils (E. Merck, Darmstadt, W.-Germany) in different solvent systems, Magnesidin has the following $R_f$-values:

| Developing agent | $R_f$-value |
|---|---|
| Benzene-acetone (1:1) | 0.54 |
| petroleum ether (60–80°C) - acetone (3:2) | 0.19 |
| benzene - ethyl acetate (1:1) | 0.15 |

The different spectral values of Magnesidin are indicated as follows:

MeOH 1 %

| UV:$\lambda_{max}$ | 257 nm ($\epsilon$ = 747.3) 1 cm |
|---|---|
| KBr IR:$\nu_{max}$ | 3500, 2925, 1709, 1669, 1637, 1618, 1560, 1470, 1380, 1300, 1260, 1190, 1175, 1140, 1090, 1005, 974, 885, 858, 797, 755, 720 cm$^{-1}$ |
| NMR:$\delta$ | (60 MHz, CDCl$_3$ + 1 drop of CD$_3$SOCD$_3$): 0.82 (t, 3H), 1.22 (m, ca. 8H), 2.18 (d, J=8Hz, 3H), 2.60 (s, 3H), 2.83 (t, 2H), 7.19 (q, J=8Hz, 1H) ppm. |

Magnesidin exhibits chemical properties which are commonly established with enolates or salts of organic acids. The Magnesium present in Magnesidin may be replaced by hydrogen according to known chemical methods, especially in the following manner:

a. By a treatment of Magnesidin with dilute inorganic or organic acids.

b. By a treatment of a Magnesidin solution, for example in methanol, with a cation exchanger, and c. by a treatment of Magnesidin with chelating agents, for example ethylene diamine tetracetic acid.

The magnesium-free form of Magnesidin is an about equivalent mixture of 1-acetyl-3-n-hexanoyl-ethylidene tetraminic acid and 1-acetyl-3-n-octanoyl-5-ethylidene tetraminic acid of the formula II

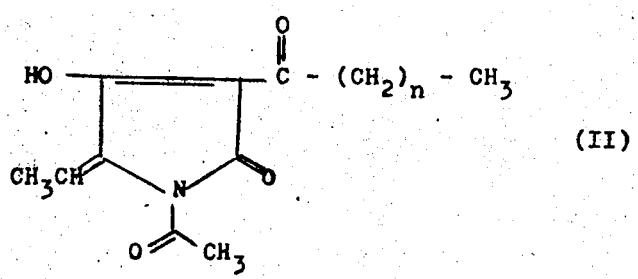

in which n stands for the integer 4 or 6, which can be established, for example, by mass spectometry. They may be separated, for example by thin-layer chromatography using kieselguhr plates, 0.25 mm thick, which are coated with paraffin and developed in a mixture of acetic acid and water (4 : 1) and treated with 5% iron chloride in 0.5 N hydrochloric acid solution for visualization purposes, whereupon two bands are obtained. The $R_f$-value of the two compounds varies within a certain range as a function of the physical parameters under which thin-layer chromatography is carried out. The average $R_f$-value of the two compounds obtained from two determinations ranges from 0.70 to 0.82. The magnesium-free form of Magnesidin is soluble in the usual organic solvents, such as benzene, methanol, ethanol, chloroform, carbon tetrachloride, ether, acetone, dimethyl-sulfoxide, dimethylformamide, pyridine, and acetic acid.

The magnesium-free form may be crystallized from organic solvents, for example methanol/water, in the form of colorless needles (m.p. 81° to 92°C). The characteristic spectral values of the magnesium-free form of Magnesidin are indicated as follows:

MeOH 1 %
UV:$\lambda_{max}$ 261 nm; ($\epsilon$ = 928.6)
1 cm
CHCl$_3$
IR:$\nu_{max}$ 3060, 2960, 2880, 1745, 1720, 1668, 1634, 1600, 1472, 1374, 1280, 1215, 1185, 1137, 1087, 1040, 994, 903, 860, 798 cm$^{-1}$.
NMR:$\delta$ (60 MHz, CCl$_4$):0.88 (t, 3H), 1.28 (m, ca. 8H) 2.20 (d, J=8Hz, 3H), 2.48 (s, 3H), 2.80 (t, J=7Hz, 2H), 7.52 (q, J=8Hz, 1H), 14.17 (broad, 1H) ppm.

The chemical properties of magnesium-free Magnesidin are associated with the structural characteristics illustrated in formula II. Magnesium-free Magnesidin gives the typical reactions commonly observed with tetraminic acids, enoles, olefins and $\alpha,\beta$-unsaturated ketones.

The antibiotic nature of Magnesidin is preserved in the magnesium-free form.

The magnesium in the antibiotic may also be replaced by monovalent cations, for example an alkali metal ion, especially sodium, potassium and lithium. These alkali metal salts may be obtained by treating the magnesium-free form until neutral with, for example, a 0.01 N solution of the corresponding alkali metal hydroxide, the cation of which is to replace the hydrogen atom. These alkali metal salts are soluble in water and preserve the antibiotic nature of Magnesidin.

The magnesium may also be replaced by other polyvalent cations, for example bivalent cations, for example copper, zinc, or alkaline earth metals, for example calcium or strontium, or trivalent cations, for example aluminum, iron, or tetravalent cations, for example tin. These salts may be obtained, for example, either (a) by treating the magnesium-free form until neutral with, for example, a 0.01 N solution of the corresponding polyvalent metal hydroxide, the cation of which is to replace the hydrogen atom, provided the polyvalent metal hydroxide is soluble in water, or (b) by treating a water-soluble Magnesidin salt, for example sodium, potassium or lithium salt with, for example, an aqueous 0.1 N solution of a water-soluble salt of the corresponding polyvalent cation, which is to replace the magnesium in Magnesidin, provided the polyvalent metal hydroxide is insoluble in water. These polyvalent salts preserve the antiobiotic nature of Magnesidin.

The LD$_{50}$ of Magnesidin administered to mice intraperitoneally is 50 mg/kg of body weight; when administered orally it is 1000 mg/kg and subcutaneously it is 1000 mg/kg.

Magnesidin has an inhibiting effect on various Gram-positive bacteria. The antibacterial spectrum of Magnesidin obtained by the series dilution test is shown in the following Table:

TABLE

| Tested strains | Minimum inhibition concentration mcg/ml |
|---|---|
| Bacillus subtilis ATCC 6633 | 3 |
| Bacillus megatherium | 2 |
| Bacillus anthracis | 2 |
| Staphylococcus aureus | 3 |
| Staphylococcus albus | 4 |
| Sarcina lutea | 2 |
| Gaffkya tetragena | 5 |
| Streptococcus faecalis | 7 |

The compounds of the invention prevent foodstuffs from perishing as caused by spore-generating organisms. They are stable to light and heat and can be heated to temperatures of about 120°C, which is essential for their use in the food industry. They can also be heated to these temperatures in autoclaves without appreciably losing their activity. Moreover, they keep their stability at alkaline pH-values, at which other antibiotics are deactivated.

This invention also relates to a pharmaceutical preparation, especially for local administration, which contains Magnesidin, the magnesium-free form thereof or a physiologically acceptable salt, in admixture or conjunction with pharmaceutically acceptable carriers, for example polyethylene glycol, vaseline, vegetable oils, starch, lactose and the like. Such a preparation may contain, for example, from about 5 to 100, preferably about 5 to 20 mg, of Magnesidin per gram of preparation.

The following Examples illustrate the invention.

I. Cultivation of the Bacteria

EXAMPLE 1

Pseudomonas magnesiorubra HPL No. Z-1190 (ATCC 21.856) was cultivated on an agar medium having the following composition:

| | |
|---|---|
| Peptone | 5.0 g |
| soluble starch | 5.0 g |
| yeast extract | 2.0 g |
| glucose | 5.0 g |
| NaCl | 30.0 g |
| agar | 20.0 g |
| distilled water | 1.0 l |
| pH | 7.4 |

The nutrient medium was sterilized by heating it to 121°C for half an hour.

The cultures were incubated for 24 hours at 28°C. A suspension of the cell material taken from a cultivating flask in 10 ml of a sterile physiological sodium chloride solution (0.85% of NaCl) was mixed with the contents of five Erlenmeyer flasks, each of 500 ml capacity, which contained 100 ml of the following nutrient solution;

| | |
|---|---|
| Glucose | 20.0 g |
| peptone | 10.0 g |
| soluble starch | 5.0 g |
| yeast extract | 2.0 g |
| NaCl | 30.0 g |
| MgSO$_4$.7 H$_2$O | 1.0 g |
| distilled water | 1.0 l |
| pH | 7.4 |

The solution was sterilized by heating it to 121°C for half an hour.

The flasks containing the inocculated culture were shaken in a rotary shaking device at 28°C and at 220 r.p.m. Every 6 hours, samples (5 ml) were taken and the bacteria cells were separated by centrifuging. The cell mass was extracted once with 1 ml of acetone and the extracts were tested by the filter blade method, *Bacillus subtilis* ATCC 6633 serving as a test organism. Optimum antibiotic production could be established after a fermenting time of 48 hours and the concentration was 500 to 600 mg of Magnesidin per liter of culture liquor. The pH-value of this liquor was 6.8 to 7.0 at the moment of isolation.

EXAMPLE 2

Pseudomonas magnesiorubra (ATCC 21.856) was cultivated in a shaking device as in Example 1 using a rotary shaker. A 24-hour culture was used as material (5% volume/volume) to be inocculated in a laboratory-scale fermenter having a capacity of 15 liters, which contained 10 l of nutrient medium of the following composition:

| | |
|---|---|
| Glucose | 20.0 g |
| peptone | 15.0 g |
| yeast extract | 5.0 g |
| soluble starch | 5.0 g |
| NaCl | 30.0 g |
| $MgSO_4 \cdot 7 H_2O$ | 1.0 g |
| distilled water | 1.0 l |
| pH | 7.4 |

The medium was sterilized by heating it to 121°C for 30 minutes.

"Desmophen" (0.05%; a reaction product of polypropylene oxide with propylene glycol, molecular weight 2000 ± 100) was added as antifoam agent. Cultivation was carried out while stirring at 28°C during 16 to 18 hours at a ventilation rate of 5 l of air per minute. Samples were taken at regular time intervals, and the antibiotic was tested as in Example 1. When cultivation was discontinued after 16 to 18 hours, the antibiotic concentration amounted to 400 – 500 mg per liter of culture solution, the pH-value thereof being between 6.8 and 7.0.

II. Isolation of Magnesidin

EXAMPLE 3

10 liters of the culture solution obtained according to Example 1 or 2 were centrifuged. The cell mass separated by centrifuging, which contained the major part of the antibiotic, was washed with a small amount of distilled water to remove adherent impurities. The cell mass was then washed four times with hot acetone, each time with 400 ml. The pink-colored acetone extract containing the antibiotic (1500 ml) was decolored using 40 g of charcoal (twice with 20 g each). The colorless acetone extract thus obtained was concentrated in vacuo to a small volume (100 ml), and, after cooling overnight in a refrigerator, the antibiotic was obtained as a reddish yellow amorphous powder. It was suction-filtered, dried (5.0 g) and extracted in a Soxhlet apparatus for 24 hours using petroleum ether (having a boiling point range of from 40° to 60°C), whereupon all colored impurities and inactive fatty material were removed. The antibiotic was then thoroughly extracted with ether. After concentration, the ether extract was a faintly colored powder which was recrystallized twice from methanol and decolored with charcoal to yield colorless crystals. Yield: 2.6 g. The biological activity of the pure antibiotic against *Bacillus subtilis* ATCC 6633 was 3 mcg/ml.

III. Magnesidin Derivatives

Replacement of Magnesium by Hydrogen

EXAMPLE 4

A Magnesidin solution (0.18 g) in 60 ml of methanol was treated while stirring for half an hour to 1 hour under a nitrogen atmosphere with 30 ml of Dowex 50 - WX 8. The methanolic solution was concentrated to dryness in vacuo, and the residue was recrystallized in a mixture of methanol and water. M.p. 81° – 92°C.

Replacement of Magnesium by MONOVALENT Cations

EXAMPLE 5

The solution obtained in Example 4, which had been treated with a cation exchanger, was again treated with a 0.01 N solution of the corresponding alkali metal hydroxide until neutral. The solvents were distilled off in vacuo, and the residue was crystallized in a mixture of benzene and acetone.

| Compound | melting point |
|---|---|
| lithium salt | 135 – 143°C |
| sodium salt | 145 – 150°C |
| potassium salt | 203 – 210°C. |

The biological activity of the magnesium-free compound and the lithium, sodium and potassium salt thereof against Bacillus Subtilis ATCC 6633 was 2.5 to 3.0 mcg/ml.

IV. Replacement of Magnesium by Polyvalent Cations

EXAMPLE 6

After treatment with a cation exchanger, the solution obtained in Example 4 was treated with a 0.01 N sodium hydroxide solution until neutral. The solution obtained was then treated with a little more than 1 equivalent of 0.1 N copper acetate, and extracted with chloroform. The chloroform extract was dried over anhydrous sodium sulfate and concentrated to dryness in vacuo. The residue was crystallized in aqueous methanol and yielded a copper salt which, during the determination of its melting point, softened at 105°C and melted at a temperature of from 200° to 225°C. The biological activity against *Bacillus subtilis* ATCC 6633 was about 3 mcg/ml.

In an analogous manner, salts may also be obtained with other polyvalent cations using, instead of copper acetate, reaction components having the desired polyvalent cation.

We claim:

1. Magnesidin, which is a mixture of compounds of the formula

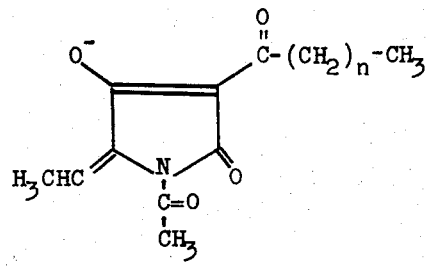

said mixture consisting essentially of about equivalent amounts of a compound wherein $n$ of said formula is 4 and of a compound wherein $n$ of said formula is 6, the corresponding magnesium-free mixture having an —OH group in the 4-position, and salts of the latter with a mono-, di-, tri-, or tetra-valent cation.

2. A salt as in claim 1 wherein said cation is a monovalent alkali metal cation.

3. A salt as in claim 2 wherein said cation is sodium, potassium, or lithium.

4. A salt as in claim 1 wherein said cation is a divalent copper, zinc, or alkaline earth metal cation.

5. A salt as in claim 4 wherein said cation is calcium or strontium.

6. A salt as in claim 1 wherein said cation is a trivalent aluminum or iron cation.

7. A salt as in claim 1 wherein said cation is a tetravalent tin cation.

* * * * *